(12) United States Patent
Shulga et al.

(10) Patent No.: US 6,825,471 B1
(45) Date of Patent: Nov. 30, 2004

(54) GAS DETECTOR AND METHOD OF OPERATING A GAS DETECTOR

(75) Inventors: Aleksandre Shulga, Muenster (DE); Udo Schmale, Rheine (DE)

(73) Assignee: Gasbeetle, Recklinghausen (DE)

( * ) Notice: Subject to any disclaimer, the term of this patent is extended or adjusted under 35 U.S.C. 154(b) by 0 days.

(21) Appl. No.: 09/936,155

(22) PCT Filed: Mar. 6, 2000

(86) PCT No.: PCT/DE00/00746
§ 371 (c)(1),
(2), (4) Date: Oct. 31, 2001

(87) PCT Pub. No.: WO00/54032
PCT Pub. Date: Sep. 14, 2000

(30) Foreign Application Priority Data

Mar. 8, 1999 (DE) .......................... 199 10 104
May 17, 1999 (DE) .......................... 199 22 590

(51) Int. Cl.[7] .............................................. G01N 21/35
(52) U.S. Cl. ...................................................... 250/343
(58) Field of Search .......................................... 250/343

(56) References Cited

U.S. PATENT DOCUMENTS

| 4,437,005 A | 3/1984 | Ophoff et al. |
| 4,914,720 A | 4/1990 | Knodle et al. |
| 5,070,244 A | 12/1991 | Simpson |
| 5,334,536 A | 8/1994 | Nonnenmacher |
| 5,464,983 A | 11/1995 | Wang |
| 5,608,219 A | 3/1997 | Aucremanne |
| 5,734,165 A | 3/1998 | Unal et al. |
| 5,874,737 A | 2/1999 | Bytyn et al. |

FOREIGN PATENT DOCUMENTS

| DE | 30 43 332 A1 | 7/1982 |
| DE | 41 11 187 C2 | 10/1992 |
| DE | 41 19 346 A1 | 12/1992 |
| DE | 44 33 336 A1 | 10/1995 |
| DE | 44 37 311 A1 | 4/1996 |
| DE | 195 25 703 A1 | 1/1997 |
| DE | 197 35 716 A1 | 2/1999 |
| EP | 0 503 511 A2 | 9/1992 |
| EP | 0 512 535 A2 | 11/1992 |
| EP | 0 794 423 A1 | 9/1997 |
| WO | WO 96/17239 A1 * | 6/1996 |

* cited by examiner

Primary Examiner—Constantine Hannaher
Assistant Examiner—Shun Lee
(74) Attorney, Agent, or Firm—Marshall & Melhorn, LLC

(57) ABSTRACT

The invention relates to an infrared gas sensor with an energy supply apparatus for operating at least one radiation source with current or voltage pulses, with at least one measurement area disposed in the beam path, with at least one wavelength-selecting element, with at least one detector element emitting an electrical measurement signal and with a switching device (3) to control the pulse duration of the current or voltage pulses.

The switching device (3) has means for setting the pulse duration in such a way that the current or voltage pulse is so turned off that the required pulse duration is smaller than that required to reach the maximum ($\tau_{max}$) of the at least one measurement signal of the at least one detector element.

13 Claims, 8 Drawing Sheets

GAS DETECTOR AND METHOD OF OPERATING A GAS DETECTOR

BACKGROUND OF THE INVENTION

Infrared gas sensors are based on the principle of the selective absorption of infrared radiation by gases. The action principle and the operating manner of infrared gas sensors may be assumed as known.

Such gas sensors generally comprise one or more radiation sources, e.g. thermal radiators such as incandescent lamps, one or more absorption sections, wavelength-selecting elements (selective radiation filters such as e.g. interference filters) and one or more radiation detectors, which convert the optical signal into an electrical measurement signal. A large number of such detectors is known from prior art. The most frequently used types of detector are inter alia pyroelectric, semiconductor (e.g. on a PbSe base) thermophile and pneumatic detectors.

A further type of embodiment is based on the alteration in pressure as a result of the heating of the gas molecules in the measurement area, which is detected by means of a microphone. The heating is caused by the absorption of the radiation energy of the radiation source(s) by the measurement gas molecules to be detected. An embodiment corresponding to prior art is disclosed in the patent DE 195 25 703 A1.

Thus, U.S. Pat. No. 5,608,219 teaches a device for detecting at least one gas with an absorption band in the infrared range, comprising a cell which contains the gas sample to be tested, an infrared radiation source, a power supply for the radiation source, an infrared radiation sensor and a measured-value evaluation unit which is secured to the sensor.

EP 512 535 teaches a portable carbon dioxide monitor in which the carbon dioxide is determined by non-dispersive infrared measurements.

EP 503 511 teach a device for the analytical determination of carbon dioxide and water through infrared analysis techniques. The gas analyzer here contains a radiation source, a sample cell and a reference cell, a detector and a gas supply.

U.S. Pat. No. 5,734,165 describes an infrared photometer which is integrated in a compact housing in which an infrared radiation source is provided with a pulse frequency of between 0.01 and 10 Hz.

U.S. Pat. No. 4,914,720 teaches a gas analyzer which is based on non-dispersive infrared photometry and with which different gases in gas mixtures can be determined.

In optical gas sensors, the radiation source is generally operated continuously (in combination with a chopper) or intermittently with a pulsed voltage. In both cases, the signal is generally detected by means of a phase-sensitive electronics (lock-in technology) or respectively an RMS converter.

The invention relates to an infrared gas sensor with an energy supply apparatus for operating at least one radiation source, for example a heat radiation source or an infrared luminescence radiation source (e.g. diode, laser diode, infrared laser), with current or voltage pulses, with at least one measurement area arranged in the beam path with at least one detector emitting an electrical measurement signal and with one switching device to control the pulse duration of the current or voltage pulses. The invention relates furthermore to a method of operating such a sensor.

In a gas sensor of this type, known from DE 30 43 332 A1, the pulse duration of the radiation source, a heat radiator, is controlled in dependence on the maximum value of the measurement signal of a radiation detector at the exit of the measuring transducer. It is proposed here that the maximum value be obtained empirically or mathematically from the course of the response curve or of the measurement signal of the measuring transducer, and that the pulse duration be controlled, by interrupting the energy supply to the heat radiator, in such a way that the maximum value lies with certainty within the pulse duration. Furthermore it is proposed that the course of the response curve be monitored by means of a maximum value detector which interrupts the energy supply or respectively the current pulse when the maximum value of the response curve is reached. With this gas sensor, a pulse/pause ratio of the energy supply of <1 and preferably between 0.1 and 0.5 can be achieved.

SUMMARY OF THE INVENTION

The object underlying the invention is to create a gas sensor of this type which has a reduced energy consumption with high measuring accuracy.

This object is achieved in relation to the sensor by the features of patent claim 1 and in relation to the method by the features of claim 9. The subordinate claims list advantageous developments.

According to the invention, therefore, the switching device is so controlled that the pulse duration is smaller than the time interval until the measurement signal has reached the maximum at $\tau_{MAX}$. This can come about by the maximum rise of the detector signal $$\left(\frac{dU_0(t)}{dt}\right)_{MAX}$$

being used as the measured value. The maximum rise of the signal is achieved substantially quicker than its maximum value: $\tau' \ll \tau_{MAX}$. Therefore the turn-on time of the radiation source $\tau_0$ in this measurement process can be substantially shorter $\tau' \leq \tau_0 \ll \tau_{MAX}$ than in all the previous ones. The pulse/pause ratio which can be thus realised is below 0.01.

The interval between individual measurements can be selected according to sensor design and application profile between a few seconds and several minutes, whereby it is possible for an operating period without a change of batteries (e.g. standard AA batteries) of more than half a year to be achieved.

This method according to the invention, like the methods according to the invention presented below, can be carried out both with a radiation detector and with an acoustic detector, such as e.g. a microphone, as the detector element. Simultaneously with a plurality of detectors, e.g. a radiation detector and a microphone, a plurality of signals can be produced, the measurement being carried out according to the invention for at least one of the two signals or also for a plurality of the signals or respectively for all the signals. When a plurality of signals is produced, the accuracy of the measurement can be further improved.

Suitable as radiation sources for infrared rays are for example incandescent lamps, thermal thin-film radiators, light emitting diodes and the like which can also be used as pulsed infrared radiation sources.

Another method of shortening the turn-on time of the radiation source, is using the measurement of the detector signal at a specific time $\tau$ after turning on the radiation source as the sensor signal, this time $\tau$ being smaller than the time of reaching the maximum value of the detector signal $\tau_{MAX}$: $\tau < \tau_{MAX}$. Preferably $\tau$ lies between the time of reaching the maximum value of the rise of the detector signal $\tau'$ and $\tau_{MAX}$: $\tau' \leq \tau < \tau_{MAX}$. As the measured value at the time $\tau$, both the instantaneous value of the detector signal $U_D(\tau)$ and the instantaneous value of its first derivative can be used $$\left(\frac{dU_D(t)}{dt}\right)_{\tau=\tau'}$$

Furthermore it is also possible to use as the measured value the period of time after the turn-on of the radiator in which a specific level of the detector signal U" or a specific spacing from the detector signal when the radiator is turned off (offset) is reached.

The period of time until a fixed rise of the detector signal is reached can also be used as the measurement signal.

Very advantageous is the operating manner of the gas sensor when the maximum rise of the detector signal $$\left(\frac{dU_D(t)}{dt}\right)_{MAX}$$

or the time at which this maximum value is reached $\tau'$ is used as the measurement signal. Here the maximum rise can be measured with the aid of a maximum value detector without giving the time of measurement.

The time $\tau'$ can be determined e.g. with the aid of a zero crossing detector from the second derivative of the detector signal.

Measuring the integral of the detector signal up to a specific point of time $\tau$, e.g. up to the maximum of the rise of the detector signal $\tau'$, is a further possible measuring method.

Preferably that is an integral over a period of time starting from the turn-on point of the radiation source ($t=0$) up to a specific time $\tau$ which is smaller than the pulse duration $\tau < \tau_0$:

$$\int_0^\tau U_D(t)dt.$$

Naturally also a plurality of the above-described methods and measured values (e.g.

$$\left(\frac{dU_D(t)}{dt}\right)_{MAX}$$

and $\tau'$) can be combined with one another to increase the sensitivity or the reliability.

The invention also relates to a method of operating an infrared gas sensor such as has been explained in detail above.

The method according to the invention is carried out in such a way that the current or voltage pulse is so turned off that the pulse duration is smaller than that required to reach the maximum ($\tau_{MAX}$) of the measurement signal of the radiation detector(s) or of the acoustic detector. Preferred embodiments of the method consist in the current or voltage pulse being turned off after a time $t=\tau$, $\tau$ lying between $t=0$ of the current or voltage pulse and $\tau_{MAX}$. It is particularly preferred if the current or voltage pulse is turned off at the maximum value of the first derivative of the measurement signal within the pulse duration. But all the embodiments previously explained in connection with the sensor can be used in the method according to the invention.

The method according to the invention has additional advantages. It is thus also possible with the method according to the invention to determine the gas concentration in a different manner. Thus the gas concentration can be determined from the value of the first derivative of the measurement signal at a specific time $\tau_{me\beta}$, which is smaller than the pulse duration or at a value of the N-th derivative (N>1) of the measurement signal at a specific time $\tau_{me\beta}$, which is smaller than the pulse duration. The gas concentration can furthermore be determined from the value of the integral of the measurement signal over a period of time starting from the turn-on time $t=0$ up to a specific time $\tau_{me\beta}$ which is smaller than the pulse duration. The first derivative can also be used for determining the gas concentration. Further preferred embodiments of the method for determining the gas concentration are quoted in claims 16 to 19.

The method according to the invention can also be used when the time constant of the detector is greater than the time constant of the radiation source used. It includes furthermore measuring methods and measuring arrangements suitable for same, in which the measurement signal dependent on the gas concentration is determined before the maximum of the detector signal is reached. In particular the pulse length of the voltage applied to the radiation source to operate same can be kept so short that the maximum of the detector signal is not reached. For frequently the kinetic course of the detector output signal, e.g. in the case of pyroelectric detectors, is determined more strongly by the properties, such as for example the time constant, of the detector itself than by the properties of the radiation source.

BRIEF DESCRIPTION OF THE DRAWINGS

In what follows a few examples of the method according to the invention of the gas sensor according to the invention are described. The figures show.

DESCRIPTION OF THE PREFERRED EMBODIMENT

Figure 1:
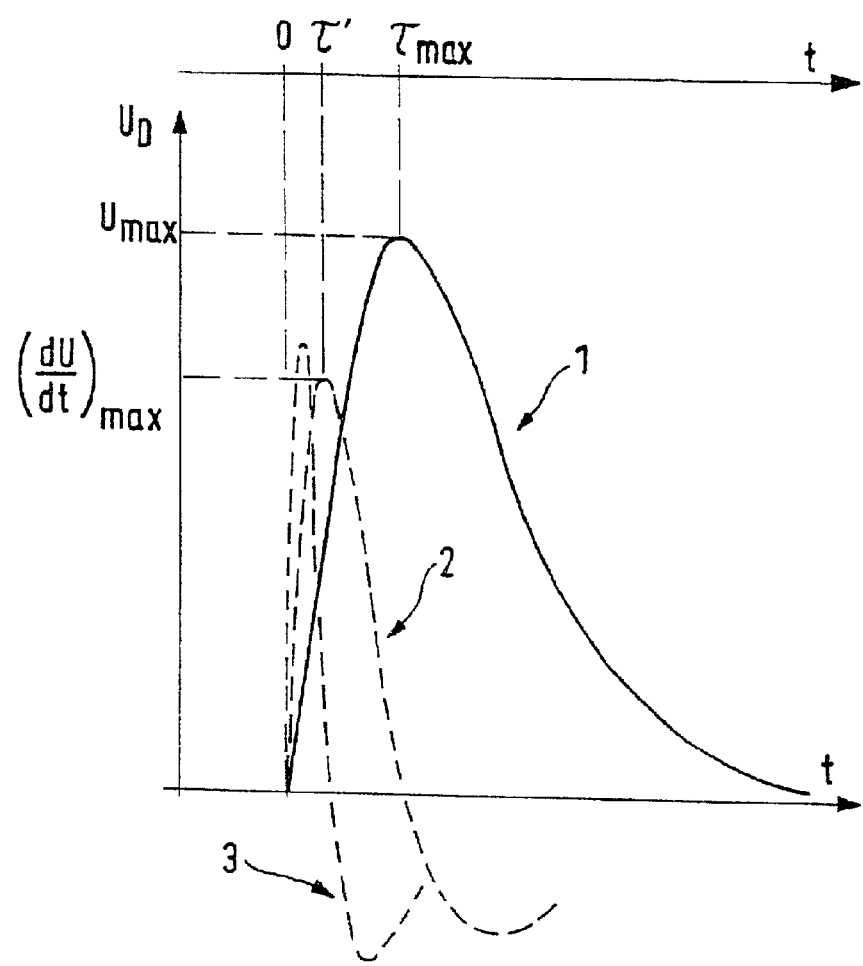
FIG. 1 a typical signal shape for a pyroelectric radiation detector.

In FIG. 1 is represented a typical signal shape for a radiation detector, here a pyroelectric detector.

The radiation source was here turned on at the time $t=0$. Curve 1 reproduces the course of the output signal of the detector (minus offset). Curves 2 and 3 show the course of the first or the second derivative.

Figure 2:
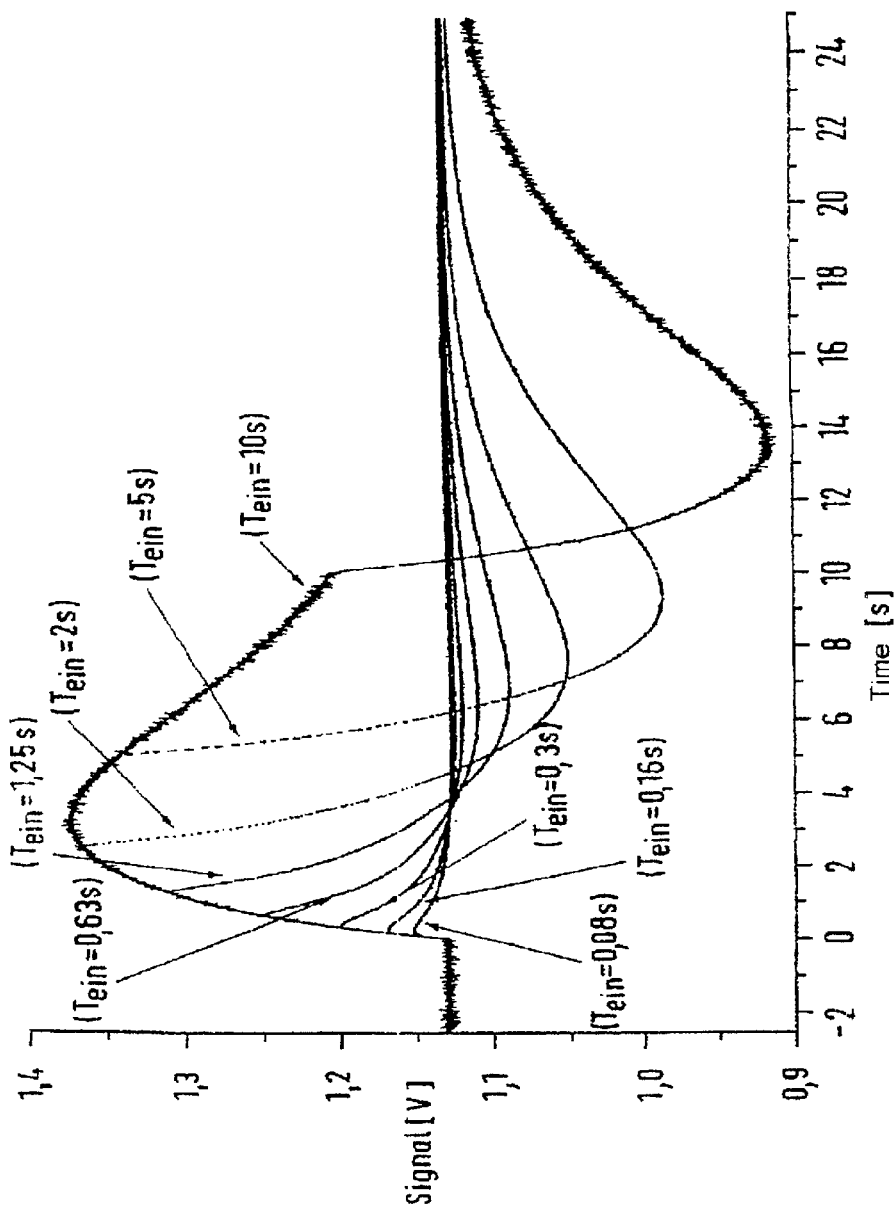
FIG. 2 a basic signal shape of a pyroelectric detector where there is a pulsed radiation source.

FIG. 2 shows the basic signal shape of a pyroelectric detector (Murata IRA410 QW1), which is exposed to the radiation of a pulsed radiation source (VCH T1 5 V, 60 mA). In FIG. 2 a group of curves is shown, the total turn-on time of the radiation source being used as a parameter. In FIG. 2 it can be recognised that the output signal of the pyroelectric detector requires approximately 2.5 seconds as a reaction to the switching on of a radiation source until it reaches its maximum. The maximum value of the first derivative of the detector signal is however reached after only 120 milliseconds (compare below, FIG. 8). If therefore the maximum value of the first derivative is used to determine the sensor signal, the radiation source can be turned off much earlier, such that the energy consumption of the radiation source is also considerably reduced. Moreover the detector signal drops after such a short radiation pulse very much quicker to its normal level, which means that higher scanning rates without significant heating of the sensor and thus without heating-up time for the sensor can be used.

Figure 3:
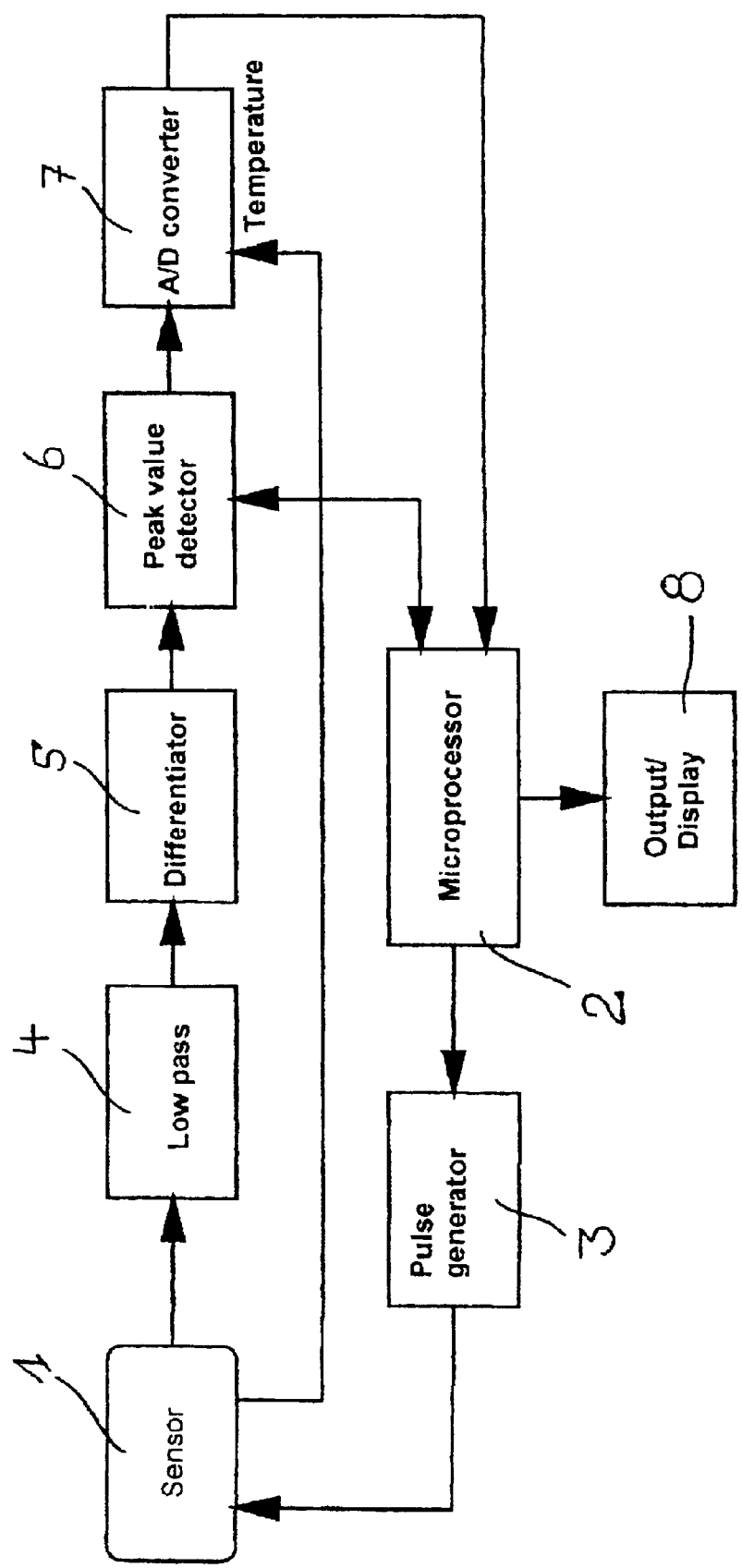
FIG. 3 a derivative circuit.

FIG. 3 shows a derivative circuit, by means of which the maximum value of the derivative of the sensor signal can be detected. In this derivative circuit, a microprocessor 2 controls a pulse generator 3 in such a way that the latter turns on the radiation source of a sensor 1 for a defined time. This time can be either rigidly set or can depend on the feedback from a peak value detector 6 to the microprocessor 2. The sensor 1 produces a measurement output signal by means of a radiation detector. This output signal passes through a low pass 4 in order to suppress higher frequency noise and a differentiator 5 in order to differentiate the measurement output signal electronically. This signal is input into a peak value detector 6, which stores the peak value of the derivatives and possibly, as described above, sends to the microprocessor 2 feedback on the attainment of the peak value. The derivative peak value detected by the peak value detector is passed to an analogue-to-digital converter 7 which converts and measures the present maximum value of the derivative of the sensor signal. Furthermore the signal of a temperature sensor contained in the sensor 1 is detected by the analogue-to-digital converter 7. Both values are then passed by the analogue-to-digital converter 7 to the microprocessor 2. The latter then resets the peak value detector and calculates from the measured values, with the aid of corresponding calibration functions, the concentration of the gas to be measured. The result is then indicated by the microprocessor 2 at an output or on a display 8.

Figure 4:
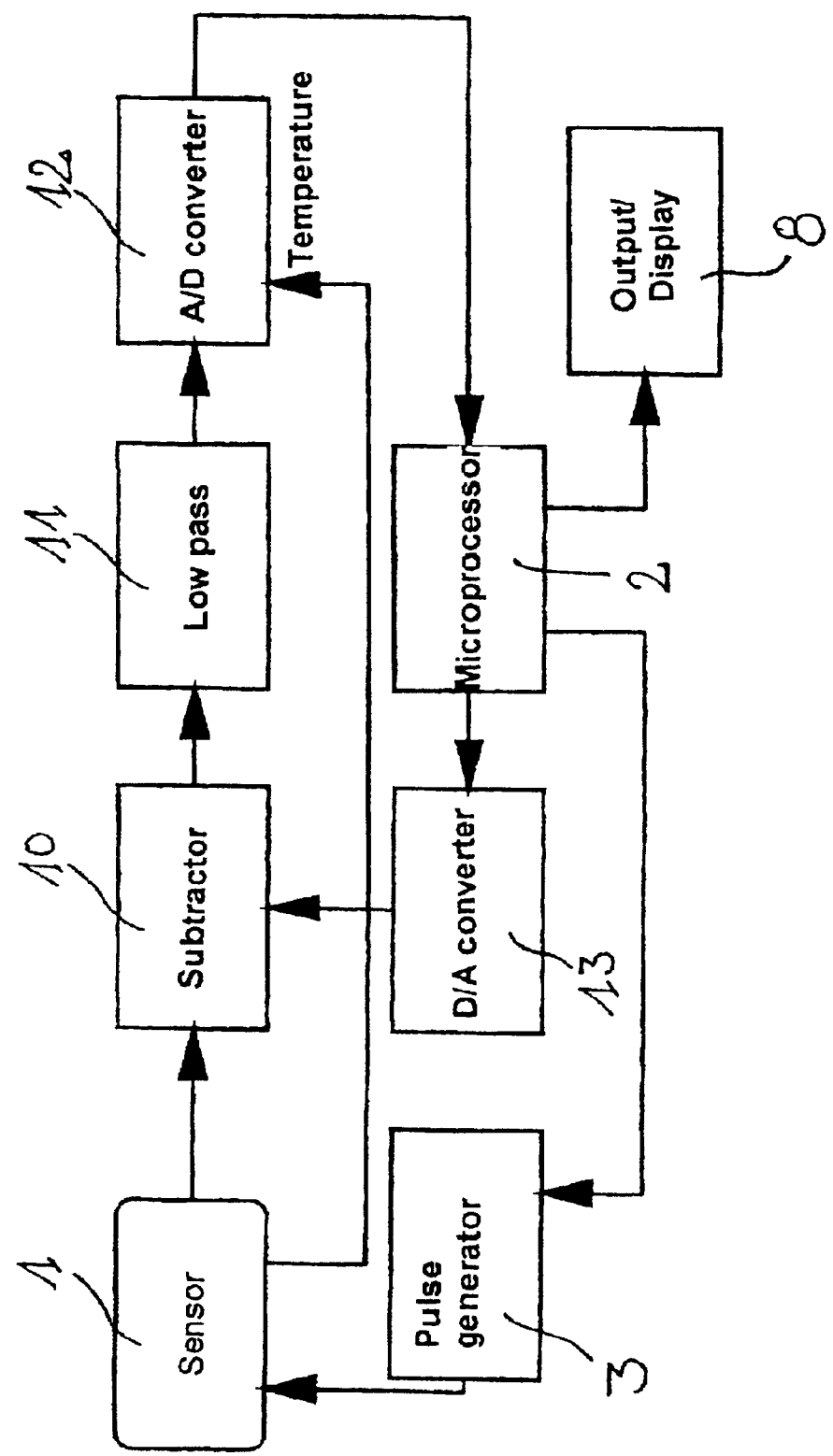
FIG. 4 a summing circuit.

FIG. 4 shows a summing circuit, in which a microprocessor 2 as in FIG. 3 drives a pulse generator 3 which turns on a radiation source of a sensor 1 for a defined time. The output signal of the radiation detector of the sensor 1 is passed to a subtractor 10, by any possible offset of the sensor signal being subtracted from the sensor signal. The voltage to be subtracted is provided to the subtractor 10 by the microprocessor 2 via a digital-to-analogue converter 13. The sensor signal thus freed of the offset is passed to a low pass 11 in which it is low-pass filtered and then received by an analogue-to-digital converter 12, converted into digital signals and passed to the microprocessor 2 which sums above a certain number of values.

If the offset of the sensor signal is temperature-dependent, it is furthermore possible to detect with the analogue-to-digital converter 12 any offset still present after the subtractor 10 before the radiation source is turned on. This comes about by the analogue-to-digital converter 12, before the radiation source is turned on, receiving the low-pass filtered offset of the sensor signal, converting it into digital signals and passing it also to the microprocessor 2, which sums above a specific number of values. The analogue-to-digital converter 12 can moreover measure the output of the temperature sensor contained in sensor 1 and pass this output to the microprocessor 2. The microprocessor 2 then calculates from the measured values, with the aid of a corresponding calibration function, the concentration of the gas to be measured.

Figure 5:
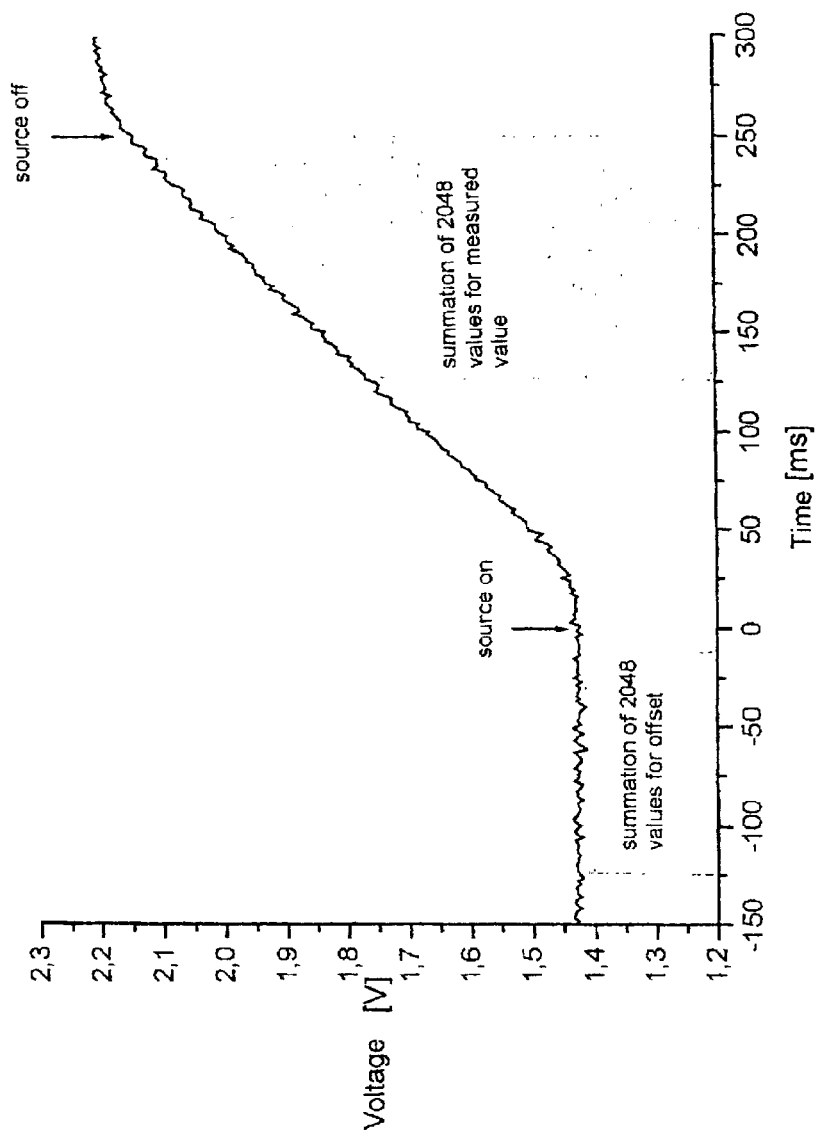
FIG. 5 the representation of a summing measurement.

FIG. 5 shows the course of a summing measurement, in which the offset of the sensor signal (detector: Murata IRA410 QW1) is determined by a summation of 2048 measurements of an analogue-to-digital converter (MAX 1246). The analogue-to-digital converter here measures at a rate of 16,000 measurements per second. These measurements come about before the light source (VCH T1 5 V, 60 mA) is turned on. After the light source is turned on, there is a pause of about 125 milliseconds and then again 2048 measurements are carried out by the analogue-to-digital converter and are added up by a microprocessor. These values then form the actual infrared measured values. To calculate the concentration of the gas to be determined, the difference from these measured values and the measured offset is evaluated with the aid of a calibrating function.

Figure 6:
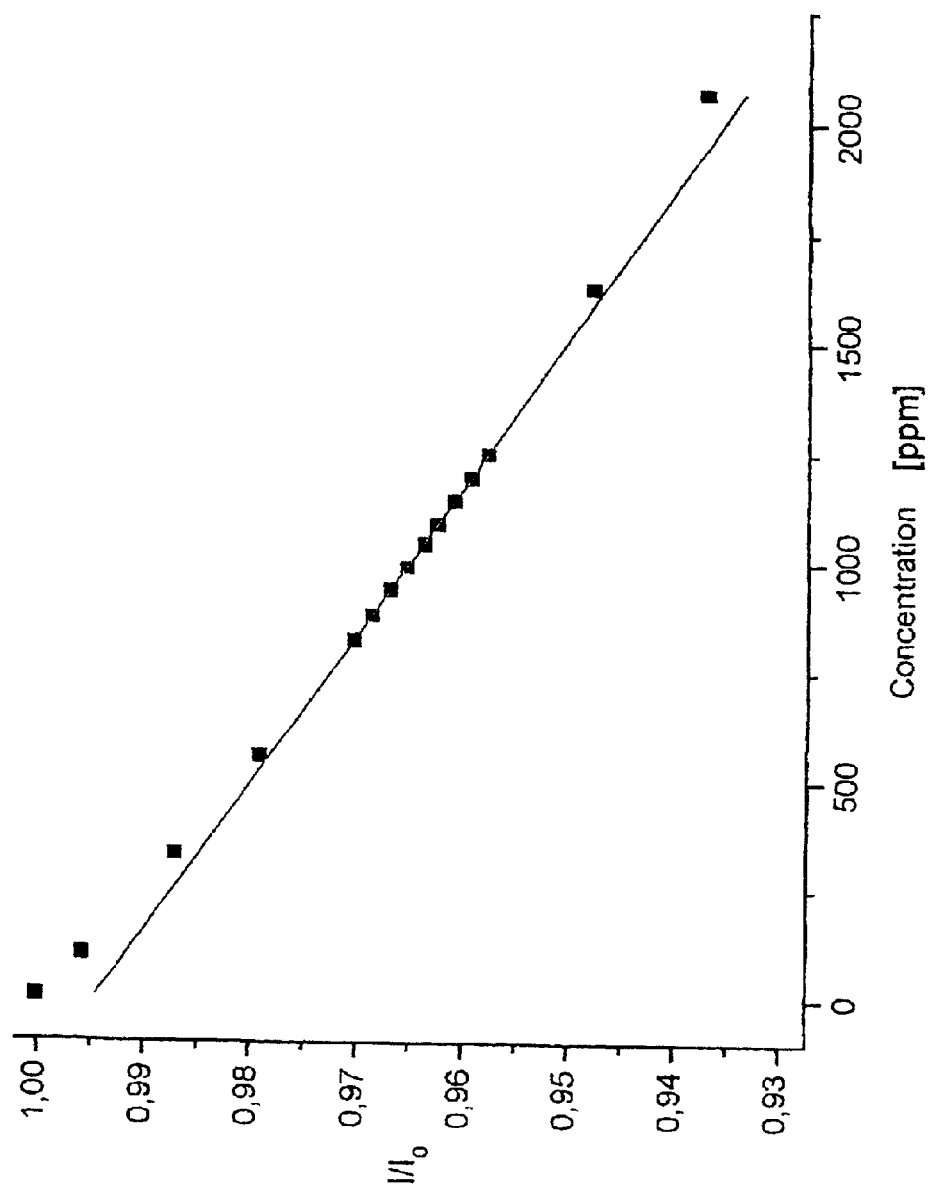
FIG. 6 a calibration curve of an infrared $CO_2$ sensor.

FIG. 6 shows the calibration curve of an infrared $CO_2$ sensor (detector: Heimann LHi 807-TC-G2; source: VCH T1 5 V 125 mA; light path 25 mm) in the range between 0 ppm and 2100 ppm $CO_2$. The linear calibration function is here optimised for the range between 800 ppm and 1200 ppm $CO_2$. This calibration curve was recorded with a derivative circuit according to FIG. 3. It can be recognised that the signal intensity has been correlated with the $CO_2$ concentration and consequently a very reliable $CO_2$ sensor has been realised.

Figure 7:
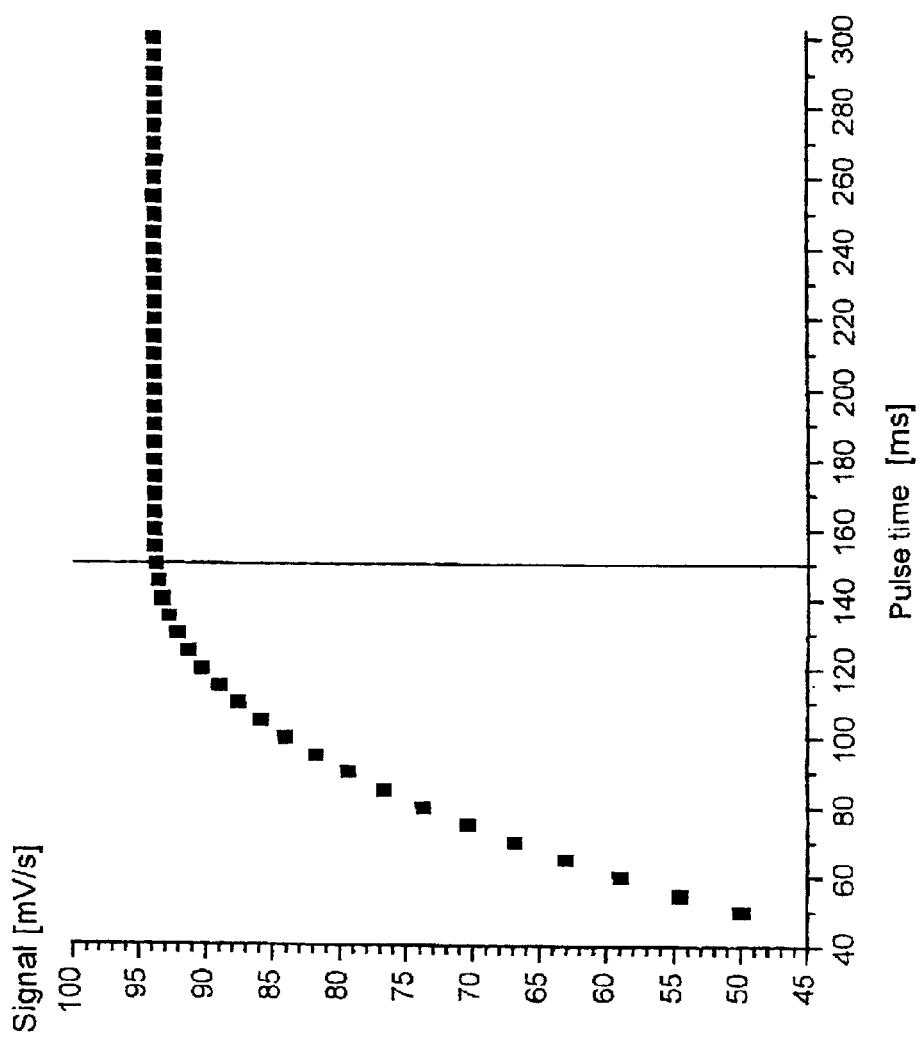
FIG. 7 the dependency of the maximum value of the derivative of a sensor signal of an infrared $CO_2$ sensor on the turn-on time of the radiation source and FIG. 8 the course of the derivatives of the sensor signal of a pyroelectric detector for very short turn-on times.

FIG. 7 shows the dependency of the maximum value of the derivatives of the detector signal of a pyroelectric infrared detector (Heimann LHi 807-TC-G2) on the turn-on period of the radiation source. A miniature incandescent lamp (VCH T1 5 V, 60 mA) was used here as the radiation source. As can be recognised, the maximum value of the derivative rises in the range between 40 milliseconds and 150 milliseconds and no longer alters the pulse duration above 150 milliseconds. Turning on the radiation source for more than 160 milliseconds thus only increases the energy consumption of the sensor, but does not contribute anything more to the concentration-dependent derivative output signal according to the invention.

Figure 8:
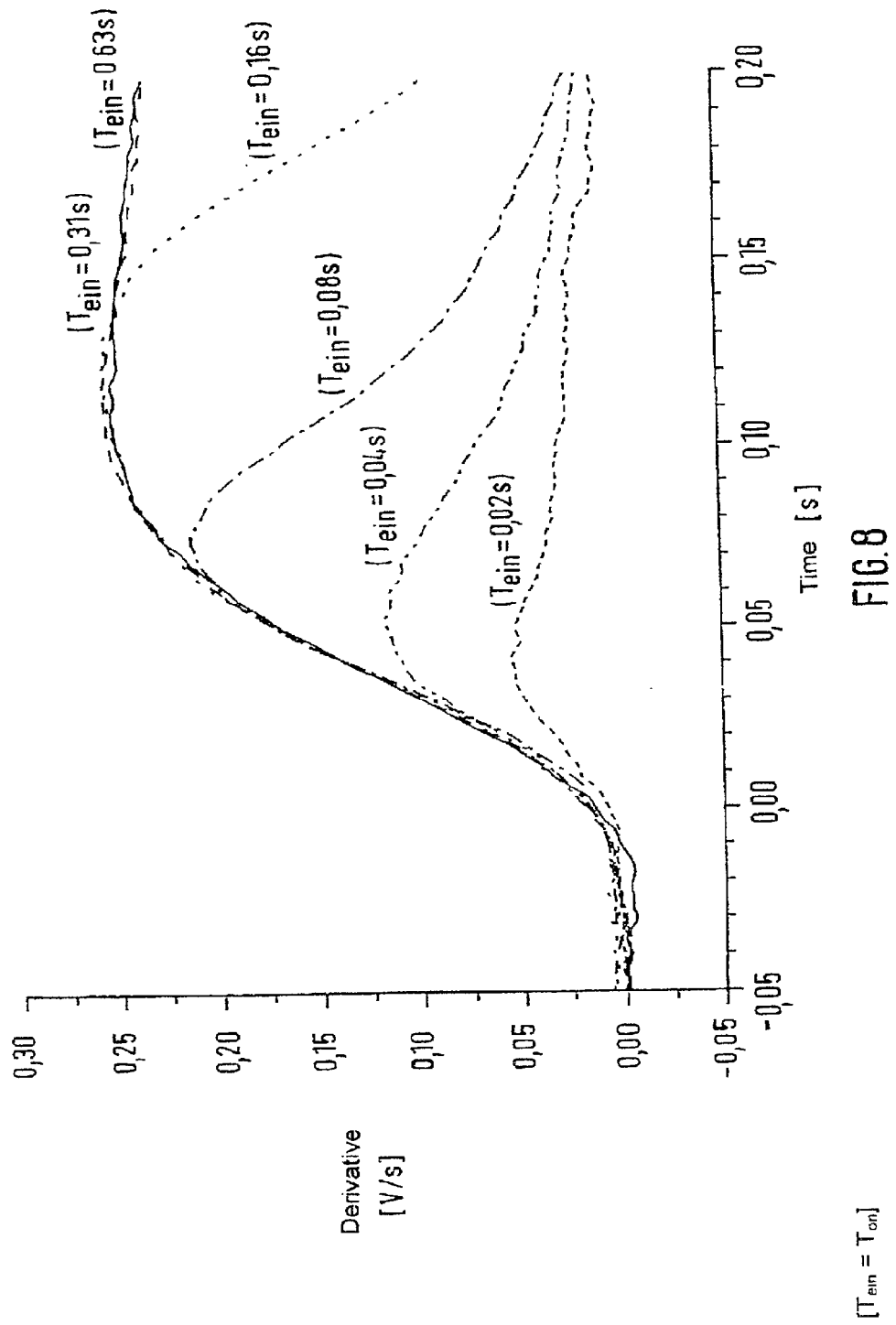

FIG. 8 shows the course of the first derivative of the detector signal of a pyroelectric detector (Murata IRA410 QW1) with very short turn-on times. FIG. 8 here shows a group of curves, the turn-on time of the light source (VCH T1 5 V 60 mA) being used as the group parameter. This amounts to between 20 milliseconds and 630 milliseconds. It can be recognised that the maximum value of the first derivative of the detector signal for a pulse duration of the light source rises from 20 milliseconds to 160 milliseconds. Longer pulse widths than 160 milliseconds do not lead to any further increase in the maximum of the first derivative of the detector signal.

What is claimed is:

1. An infrared gas sensor with an energy supply apparatus for operating at least one radiation source with current or voltage pulses, with at least one detector element emitting an electrical measurement signal, with at least one wavelength-selecting element located between the at least one radiation source and the at least one detector element, and with at least one measurement area arranged between the at least one radiation source and the at least one detector element and disposed in the beam path, and with a switching device to control the pulse duration of the current or voltage pulses, wherein the switching device has means for setting the pulse duration in such a way that the current or voltage pulse is turned off in a manner such that the pulse duration is smaller than the required to reach the maximum ($\tau_{MAX}$) of the at least one measurement signal of the at least one detector element and such that the turn-off takes place when a specific measurement signal value is reached within the pulse duration or the turn-off occurs when a specific value of the first derivative of the measurement signal is reached within the pulse duration or the turn-off occurs when the maximum value of the first derivative of the measurement signal is reached within the pulse duration or the turn-off occurs when a specific value of the integral of the measurement signal over a time interval, starting from the tun-on time t=0 is reached within the pulse duration.

2. An infrared gas sensor according to claim 1, wherein the at least one detector element is at least one of a radiation detector, a pressure transducer and a microphone.

3. An infrared gas sensor according to claim 1, wherein the current or voltage pulse is turned off after a specific time t=τ, the time τ lying between the turn-on time t=0 of the current or voltage pulse and $\tau_{MAX}$.

4. An infrared gas sensor according to claim 1, wherein the switching device is so operated that a pulse/pause ratio of less than 0.01 is set.

5. A method for operating an infrared gas sensor according to claim 1, wherein the current or voltage pulse is turned off in a manner such that the pulse duration is smaller than that used to reach the maximum ($\tau_{MAX}$) of the measurement signal of the at least one detector element and such that the turn-off takes place when a specific measurement signal value is reached within the pulse duration or the turn-off occurs when a specific value of the first derivative of the measurement signal is reached within the pulse duration or the turn-off occurs when the maximum value of the first derivative of the measurement signal is reached within the pulse duration or the turn-off occurs when a specific value of the integral of the measurement signal over a time interval, starting from the turn-on time t=0 is reached within the pulse duration.

6. A method according to claim 5, wherein, to determine the gas concentration, the value of the first derivative of the measurement signal at a specific time $\tau_{meß}$ which is smaller than the pulse duration, is used.

7. A method according to claim 5, wherein, to determine the gas concentration, the value of an N-th derivative (N>1) of the measurement signal at a specific time $\tau_{meß}$ which is smaller than the pulse duration, is used.

8. A method according to claim 5, wherein to determine the gas concentration the value of the integral of the measurement signal over a period of time starting from the turn-on point t=0 up to a specific time $\tau_{meß}$ which is smaller than the pulse duration, is used.

9. A method according to claim 5, wherein to determine the gas concentration, the maximum value of the first derivative of the measurement signal is used.

10. A method according to claim 5, wherein, to determine the gas concentration, at least one of the times, is used at which a specific value of the measurement signal, of the N-th derivative (N>1) of the measurement signal or of the integral of the measurement signal is reached.

11. A method according to claim 5, wherein, to determine the gas concentration, the time at which the maximum value of the first derivative of the measurement signal is reached, is used.

12. A method according to claim 5, wherein, to determine the gas concentration, the time of the first zero crossing of the second derivative of the measurement signal is used.

13. A method for operating an infrared gas sensor according to claim 5, to determine the concentration of a gas, comprising evaluating the results of at least two tests of the same measurement signal, said at least two tests being selected from the group consisting of:

a) using the value of the measurement signal at a specific time $\tau_{meß}$, which is smaller than the pulse duration;

b) using the value of the first derivative of the measurement signal at a specific time $\tau_{meß}$, which is smaller than the pulse duration;

c) using the value of an N-th derivative (N>1) of the measurement signal at a specific time $\tau_{meß}$, which is smaller than the pulse duration;

d) using the value of the integral of the measurement signal over a period of time starting from the turn-on point t=0 up to a specific time $\tau_{meß}$, which is smaller than the pulse duration;

e) using the maximum value of the first derivative of the measurement signal;

f) using at least one of the times, at which a specific value of the measurement signal, of the N-th derivative (N>1) of the measurement signal or of the integral of the measurement signal;

g) using the time at which the maximum value of the first derivative of the measurement signal is reached; and h) using the time of the first zero crossing of the second derivative of the measurement signal.

* * * * *